(12) United States Patent
Custance et al.

(10) Patent No.: US 6,238,910 B1
(45) Date of Patent: May 29, 2001

(54) THERMAL AND FLUID CYCLING DEVICE FOR NUCLEIC ACID HYBRIDIZATION

(75) Inventors: Aaron Custance, Walden; Jonathan I. Parker, Huntingdon, both of (GB)

(73) Assignee: Genomic Solutions, Inc., Ann Arbor, MI (US)

( * ) Notice: Subject to any disclaimer, the term of this patent is extended or adjusted under 35 U.S.C. 154(b) by 0 days.

(21) Appl. No.: 09/371,107

(22) Filed: Aug. 10, 1999

Related U.S. Application Data (60) Provisional application No. 60/096,109, filed on Aug. 10, 1998.

(51) Int. Cl.[7] .................................................. C12M 1/40
(52) U.S. Cl. ................................... 435/287.2; 435/286.5; 435/286.1; 435/288.3
(58) Field of Search ..................... 435/6, 286.1, 286.5, 435/287.2, 288.3

(56) References Cited

U.S. PATENT DOCUMENTS

| | | | |
|---|---|---|---|
| 4,753,775 | * | 6/1988 | Ebersole et al. ................. 422/81 |
| 4,847,208 | * | 7/1989 | Bogen ............................. 436/174 |
| 5,273,905 | * | 12/1993 | Muller et al. ..................... 435/301 |
| 5,436,129 | * | 7/1995 | Stapleton ........................... 435/6 |
| 5,589,136 | * | 12/1996 | Northrup et al. ................. 422/102 |

FOREIGN PATENT DOCUMENTS

| | | | |
|---|---|---|---|
| 0 270 363 | * | 6/1988 | (EP) . |
| 96/30124 | * | 10/1996 | (WO) . |

* cited by examiner

*Primary Examiner*—William H. Beisner
(74) *Attorney, Agent, or Firm*—Rader, Fishman & Grauer PLLC (57) ABSTRACT

An apparatus for automatically hybridizing nucleic acid samples is disclosed. The apparatus includes a fluid control module and a temperature control module for precisely controlling fluid contacting and temperature of a plurality of DNA samples. The DNA samples are typically arrayed on solid substrates (glass microscope slides), and the disclosed apparatus can process up to twelve slides at one time on a master unit; satellite units can be added to increase the number of slides. All slides can be processed in parallel, or may be addressed individually to undergo different hybridization protocols. Thermal control is typically by slide pairs, such that each slide pair undergoes the same temperature profile. Processes are carried out under software control by an embedded PC (personal computer). User input is by touchscreen, floppy disk drive, or external network control.

44 Claims, 11 Drawing Sheets

THERMAL AND FLUID CYCLING DEVICE FOR NUCLEIC ACID HYBRIDIZATION

This application claims the benefit of U.S. Provisional Application No. 60/096,109, filed Aug. 10, 1998.

BACKGROUND OF THE INVENTION

1. Field of the Invention

This invention relates to devices and processes for hybridizing nucleic acid samples, and more particularly, to an automated device for hybridizing DNA microarrays.

2. Discussion

Use of DNA (deoxyribonucleic acid) microarrays provides a powerful technique to analyze expression of thousands of genes simultaneously. The technique includes immobilizing DNA samples from large numbers of genes on a solid substrate, such as a glass microscope slide. The DNA samples appear as an array of spots on the substrate, and one can determine the origin of a particular DNA sample by knowing its position in the array. The technique typically provides contacting the DNA microarray with RNA (ribonucleic acid) probes to detect specific nucleotide sequences in the DNA samples. To distinguish between different RNA probes, each is labeled with a tag that fluoresces at a wavelength that is unique for the particular probe.

Under proper conditions, the RNA probes will hybridize or bind to the immobilized DNA samples, resulting in hybrid DNA-RNA strands. For each of the immobilized DNA samples, and for a particular RNA probe, one can discern differences in hybridization among DNA samples by measuring the intensity and the wavelength dependence of fluorescence of each microarray element. In this way, one can determine whether gene expression levels vary among DNA samples. Thus, using DNA microarrays, one can learn much about expression of a large number of genes, and about comprehensive patterns of gene expression, using relatively small amounts of biological material.

Although DNA microarrays are powerful tools, instruments currently available to hybridize DNA microarrays need improvement. Most instruments that can process DNA microarrays have rudimentary temperature control. But nucleic acid hybridization demands precise temperature control. Rates of hybridization and equilibrium concentrations of hybrid DNA-RNA strands depend strongly on temperature and therefore accurate comparisons among hybridization experiments require that the experiments be run at the same temperature. In addition, precise temperature programming during an experiment is often critical to minimizing spurious probe-sample binding. For example, rapidly decreasing temperature following hybridization—a process called step-wise probe annealing—reduces background binding.

Generally, instruments that can process DNA microarrays also lack an adequate system for controlling fluid contacting. During hybridization, the DNA microarray is immersed in a fluid that contains the RNA probes. The rate at which the probes bind to the DNA samples will depend, in part, on the concentration of the probes. However, the concentration of the probes near the immobilized DNA samples may be much different than the bulk concentration of the probes. Although agitating the fluid helps minimize concentration gradients between the bulk fluid and fluid next to the substrate surface, excessive fluid mixing may create high shearing and normal forces that may dislodge the DNA samples.

The present invention overcomes, or at least reduces, one or more of the problems set forth above.

SUMMARY OF THE INVENTION

The present invention provides a DNA hybridization apparatus capable of precise thermal and fluid control. The present invention is particularly useful when used in conjunction with DNA spotted glass slides (DNA microarrays). The apparatus can also be used for hybridizing other materials on other substrates. Multiple slides can be processed at one time (in parallel) or in rapid serial fashion. A fluid manifold allows for control of multiple fluids across the surface of each slide. All slides can contact the same sequence of fluids or may undergo different fluid contacting protocols. Thermal control is typically by slide pair, so that each slide pair undergoes the same temperature profile or different pairs can have different temperature programming. Small volumes of liquids can be manually applied to each of the slides. Each slide pair is provided with separate clamping mechanisms to seal DNA sample areas of each slide. Fluids are moved under negative pressure throughout the instrument, ensuring that no dangerous chemicals can be ejected under pressure. The present invention also provides for software control of fluid contacting and sample temperature using software running on an embedded personal computer. User input is by touchscreen floppy disk drive or external connection to a system network. The system network distributes control signals and software instructions between master and satellite fluid control units and thermal control modules for each of the slide pairs.

DETAILED DESCRIPTION

Overview

Figure 1:
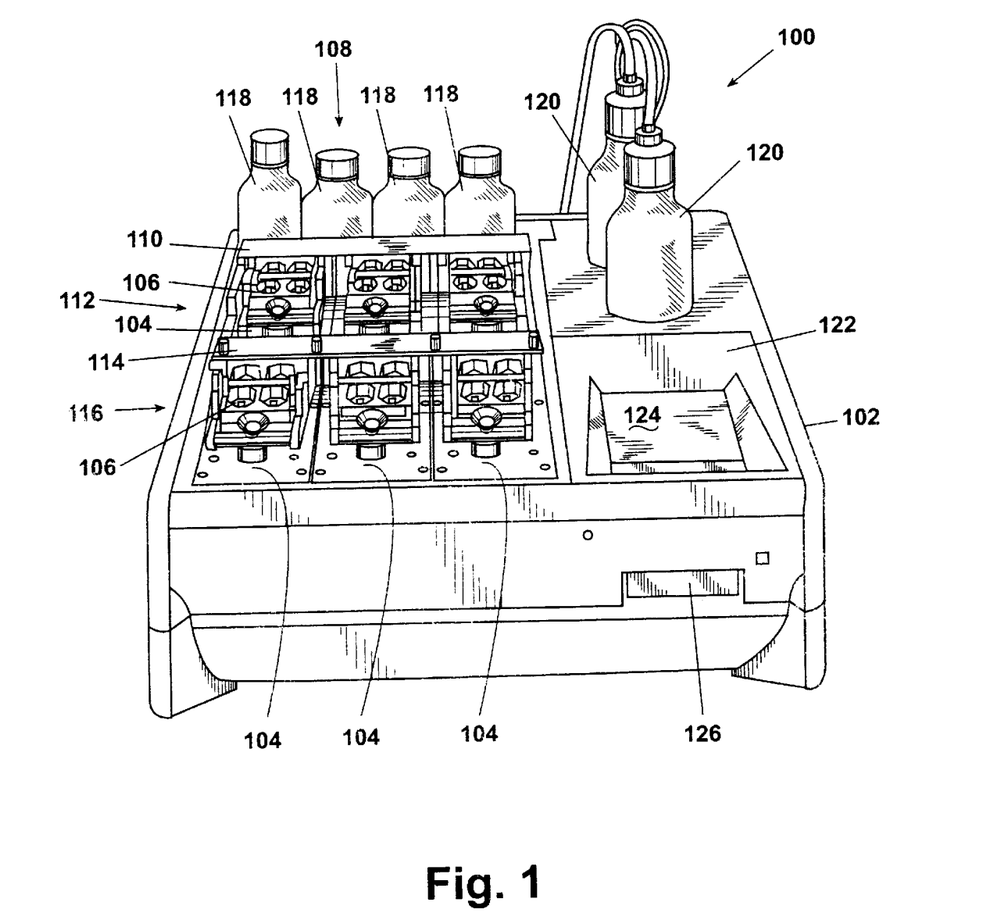
FIG. 1 shows a perspective front view of one embodiment of an automated DNA hybridization apparatus for use with DNA microarrays.

FIG. 1 shows a perspective front view of one embodiment of an automated DNA hybridization apparatus 100 for use with DNA microarrays (glass microscope slides spotted with DNA). The apparatus 100 shown in FIG. 1 includes a housing 102 that contains six thermal management modules 104, though the number of thermal management modules 104 can vary. Each of the thermal management modules 104 controls the temperature of one of six slide plate assemblies 106. Each of the slide plate assemblies 106 includes a pair of glass microscope slides (not shown) spotted with DNA. During processing, each pair of glass microscope slides can undergo different temperature programming since the thermal management modules 104 can operate independently.

During hybridization, a fluid control module 108 distributes various liquids (buffers, reagents, and the like) and various gases (air, for example) to each glass slide. The fluid control module 108 includes a master manifold 110, which is in fluid communication with a first row 112 of slide plate assemblies 106, and a satellite manifold 114, which is in fluid communication with a second row 116 of slide plate assemblies 106. The master manifold 110 and the satellite manifold 114 contain valves and conduits (not shown) that allow fluid flow from liquid reservoirs 118 to individual glass slides. In addition, the master manifold 110 and the satellite manifold 114 allow fluid flow from individual glass slides to waste containers 120. Use of two waste containers 120 obviates the need to mix reactive wastes or to change collection vessels during processing. As described below, each of the DNA microarrays may contact the same or different fluids during hybridization. A pump (not shown) maintains vacuum within headspaces of the two waste containers 120. Ambient pressure in the liquid reservoirs 118 and vacuum within the waste containers 120, results in a pressure drop that drives fluid flow throughout the fluid control module 108. Since all fluid contacting within the apparatus 100 occurs at below-ambient pressure, no dangerous chemicals can be ejected from the apparatus 100 under pressure.

Thermal management and fluid contacting are under the control of software running on an embedded personal computer (PC) module 122. User input is by touchscreen 124 or a floppy disk drive 126. A proprietary system network distributes control signals and software instructions among the thermal management modules 104 for each of the slide plate assemblies 106. The system network also supports external connection to other satellite units, which include slide pairs, fluid control modules, and thermal management modules. The user can program processing steps on the apparatus 100 via application software and either touchscreen 124 or floppy disk drive 126. Process control programs entered on the touchscreen 124 can be stored on the embedded PC module 122 hard drive or downloaded to the floppy disk drive 126.

Though not shown in FIG. 1, the apparatus 100 also includes a power supply module. The power supply module provides current to actuate valves on the master 110 and satellite 114 manifolds, and provides energy to power each of the thermal management modules 104. Because line voltage limits available current to about 10 amps, the power supply module cannot provide power to all of the thermal management modules 104 simultaneously without severely diminishing heating or cooling rate. Instead, the power supply module uses intelligent energy scheduling by first providing power to one or two of the slide plate assemblies 106. After they attain their desired temperatures, the power supply module provides power to a second group of slide plate assemblies 106. This process continues until all of the slide plate assemblies 106 reach their desired temperatures.

Fluid Control Module

Figure 2:
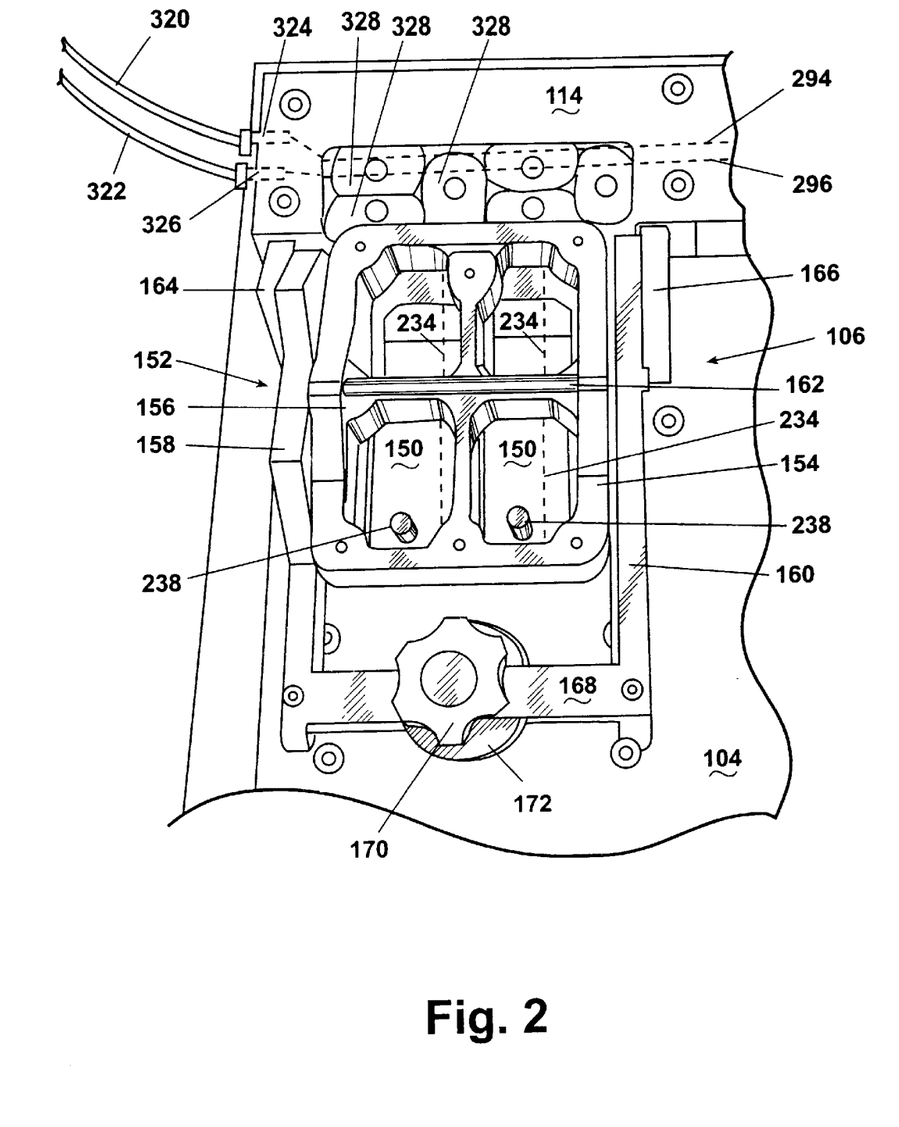
FIG. 2 shows a perspective top view of one of a slide plate assembly.
Figure 3:
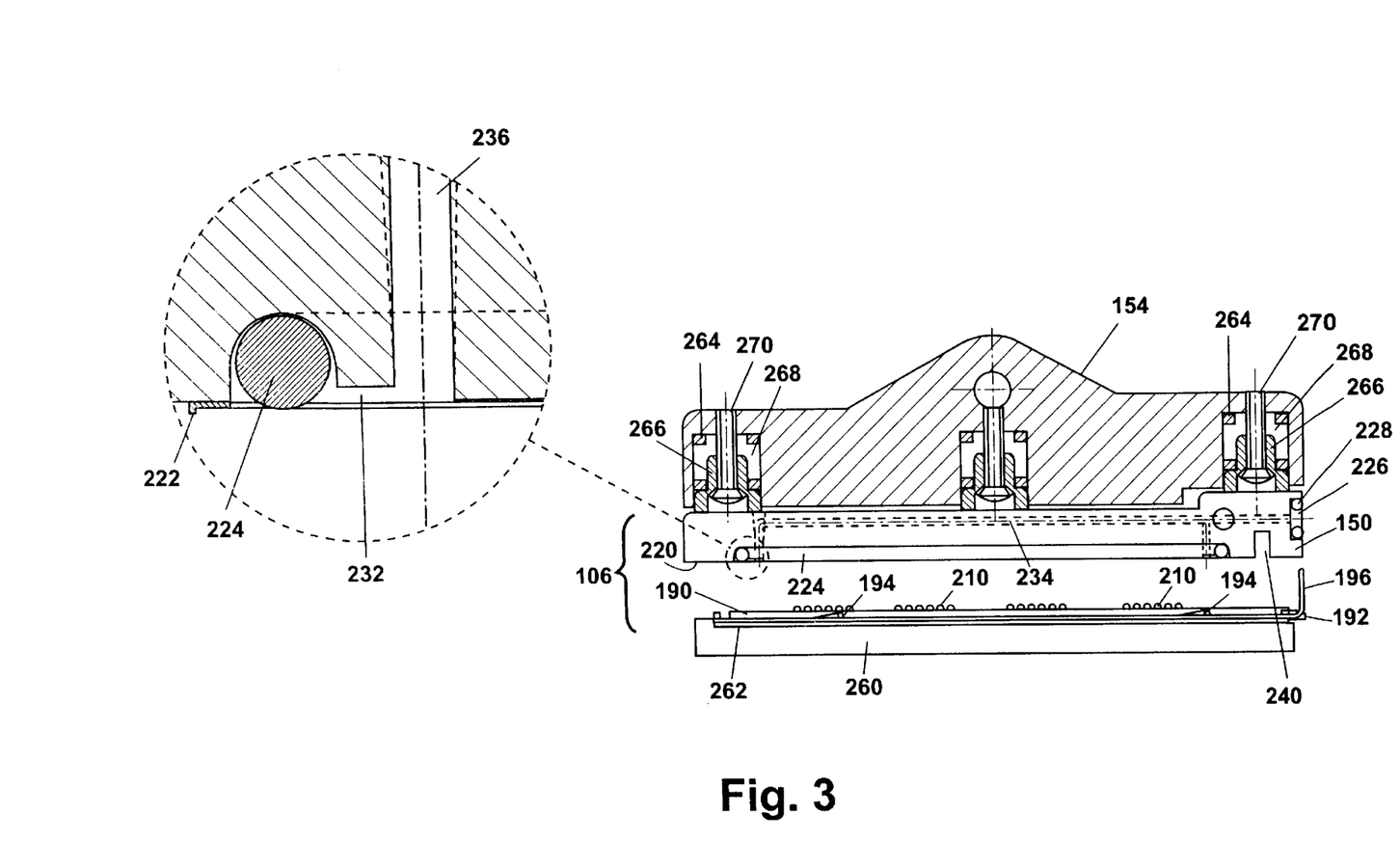
FIG. 3 shows a cross-sectional side view of a slide plate assembly and clamp.

FIG. 2 and FIG. 3 show, respectively, a perspective front view and cross-sectional side view of one of the slide plate assemblies 106. As shown in FIG. 2, the slide plate assembly 106 includes a slide cover 150 that is held in place with a clamp 152. The clamp 152 is a generally rectangular frame 154 having a single, mid-span cross member 156. The rectangular frame 154 is mounted on a pair of clamp arms 158, 160 using a cylindrical rod 162 that allows the rectangular frame 154 to pivot about the centerline of the cylindrical rod 162. First ends of the clamp arms 158, 160 are pivotably mounted on hinges 164, 166, which are fastened to the thermal management module 104; a rectangular bar 168 attached to second ends of the clamp arms 158, 160 prevents relative movement of the clamp arms 158, 160. To secure the slide plate assembly 106, a knob 170, which is mounted on the rectangular bar 168, is threaded into a clamp base 172 which is attached to the thermal management module 104.

As shown in FIG. 3, the slide plate assembly 106 includes a slide cover 150 disposed above a pair of glass slides 190 that are contained on a planar, stainless steel slide carrier 192. During processing, the slide cover 150 is disposed on the glass slides 190. The slide carrier 192 positions the glass slides 190 using a series of cut out tabs 194 that are bent upward at an angle of about 10 degrees. The cut out tabs 194 allow for slight variations in dimensions of the glass slides 190. A U-shaped tab 196 located at one end of the slide carrier 192 engages a locator pin (not shown) on the manifolds 110, 114 shown in FIG. 1 to fix the position the glass slides 190 and the slide carrier 192 in the apparatus 100.

Figure 4:
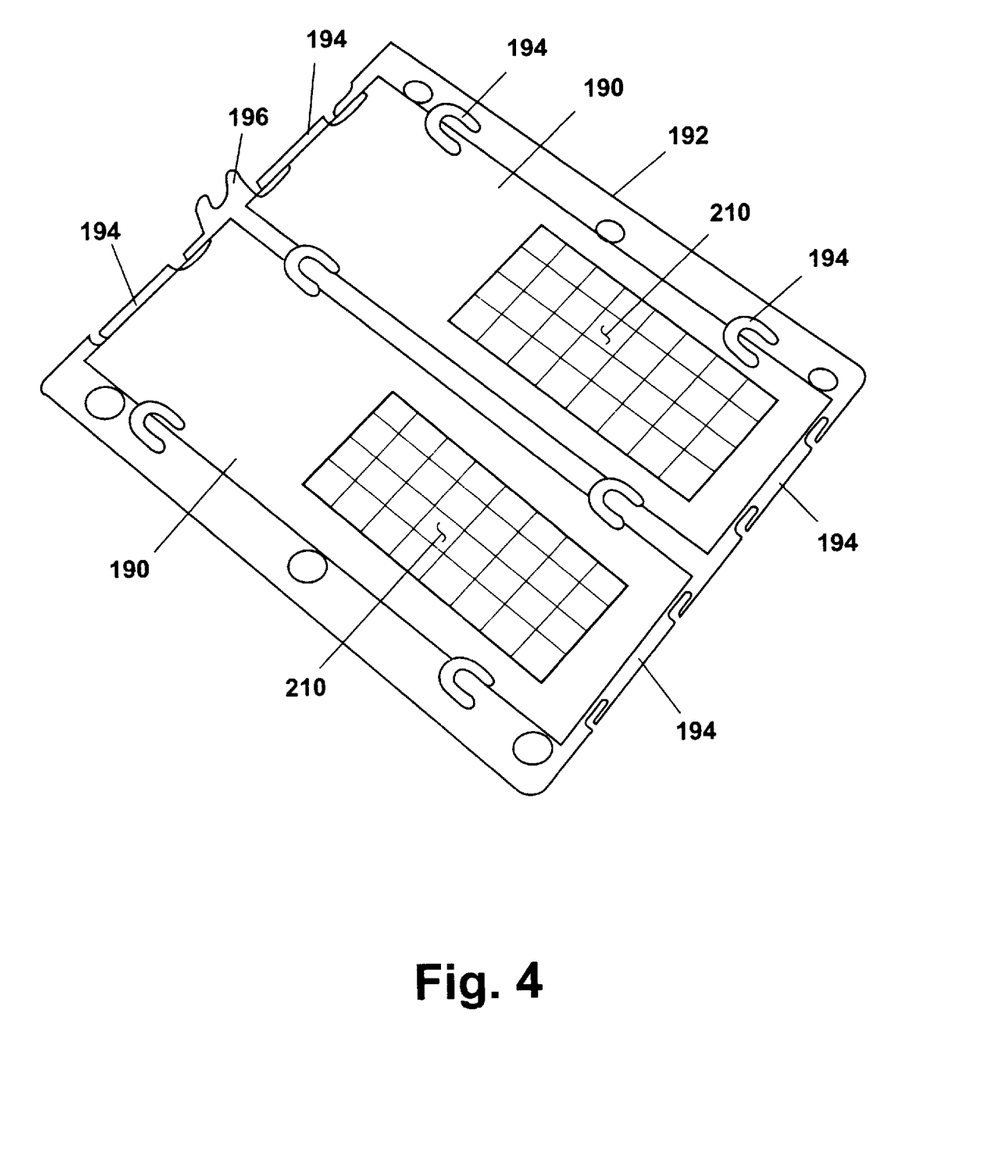
FIG. 4 shows a perspective top view of a slide carrier and the pair of glass slides (DNA microarrays).
Figure 5:
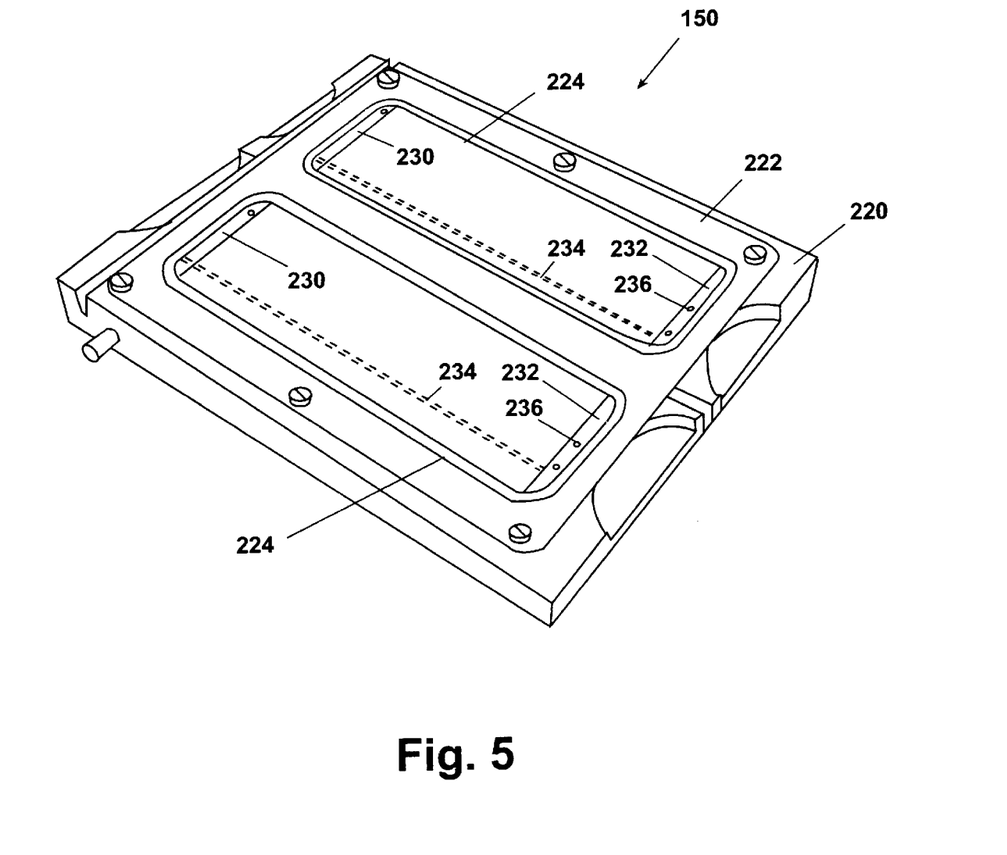
FIG. 5 shows a perspective bottom view of a slide cover.

Further details of the slide plate assembly 106 are shown in FIG. 4 and FIG. 5. FIG. 4 shows a perspective top view of the slide carrier 192 and the pair of glass slides 190. Each of the glass slides 190 is spotted with DNA in the form of an array 210.

FIG. 5 shows a perspective view of a bottom surface 220 of the slide cover 150. The slide cover 150 is constructed from a high temperature plastic to prevent sagging or softening at the higher operating temperatures of the apparatus 100. A suitable plastic includes polysulfone. Polysulfone possesses the requisite temperature characteristics and is transparent, which allows direct viewing of the glass slides 190 during processing. In addition, the absorption and attenuation characteristics of polysulfone help prevent photo bleaching of the DNA microarray, RNA probes, and the like during processing.

A shim 222, having a pair of rectangular cut outs of slightly smaller dimension than the glass slides 190, is disposed on the bottom surface 220 of the slide cover 150. The thickness of the shim 222 defines a standoff between the bottom surface 220 of the slide cover 150 and the glass slides 190. Two perfluoroelastomer o-rings 224, which are inert and will not bind to nucleic acids, are placed in grooves cut into the bottom surface 220 of the slide cover 150 around the inner periphery of the shim 222. During processing, the bottom surface 220 of the slide cover 150 is disposed on the glass slides 190, compressing the o-rings 224 and defining two slide cavities for fluid flow.

Referring to FIG. 3 and FIG. 5, fluid enters and exits each of the slide cavities through if ports 226 located at one end of the slide cover 150. The ports 226 provide fluid connections with manifolds 110, 114 shown in FIG. 1, and are sealed with o-rings 228. For each slide cavity, fluid enters one of the ports 226 into a first lateral diffusion channel 230 that is cut into the slide cover 150. Next, fluid flows the length of the cavity along the surface of the slide 190 and dumps into in a second lateral diffusion channel 232. From the second diffusion channel 232, fluid flows within a return channel 234 bored in the slide cover 150 back towards the ports 226, and exits the slide cavity through one of the ports 226. Note that, in addition to diffusing flow, which helps prevent DNA shearing, the diffusion channels 230, 232 act as small fluid reservoirs that empty and fill as the temperature within the slide cavity rises and falls.

As shown in FIG. 3 and FIG. 5, the slide cover 150 contains two injection ports 236 for manually injecting small liquid volumes (of RHA probe, say) directly into each of the slide cavities. The injection ports 236 are drilled with a taper that matches the profiles of an injection device—typically a pipette—and polyethylene plugs 238 that, as shown in FIG. 2, seal the ports 236 when not in use. The taper does not allow fluid to remain in the injection ports 236 once the plugs 238 are inserted, thus reducing the apparent volume of the slide cavity and conserving RNA probe.

During manual injection, liquid is drawn into the second diffusion channel 232 by capillary action and flows across the surface of the slide 190 within the slide cavity until the liquid reaches the first diffusion channel 230. Because manual liquid injection occurs at the second diffusion channel 232, and the slide plate assembly 106 tilts slightly upward (about 10 degrees or so) towards the first diffusion channel 230, the liquid displaces and expels air within the slide cavity out of the ports 226 during injection. Liquid should not completely fill both diffusion channels 230, 232 since they are designed to compensate for thermal expansion and contraction of the fluid within the slide cavity.

Thermal breaks 240, such as the one shown in FIG. 3, are cut into the slide cover 150 to reduce the distortion resulting from thermal gradients in a direction parallel to the bottom surface 220 of the slide cover 150. Since the thermal breaks 240 improve flexibility, they also allow the slide cover 150 to conform to any irregularities in flatness. Distortion arising from thermal gradients in a direction perpendicular to the surface 220 of the slide cover 150 are reduced by making the slide cover 150 thinner and by reducing its thermal mass.

Referring once again to FIG. 3, during processing, the clamp 152 presses the slide plate assembly 106 against elements of the thermal management module 104—thermal plate 260 and thermal pad 262—using spring 264 loaded contact ferrules 266 mounted in recesses 268 in the clamp frame 154. The contact ferrules 196 are slidably mounted on screws 270 threaded into the clamp frame 154. The contact ferrules 266 are arranged around the clamp frame 154 so they exert a downward force that is evenly distributed along the periphery of the slide cover 150. The applied pressure is sufficient to ground out the shim 222 against the glass slides 190 and to prevent warping of the slide cover 150 due to thermal gradients.

Figure 6:
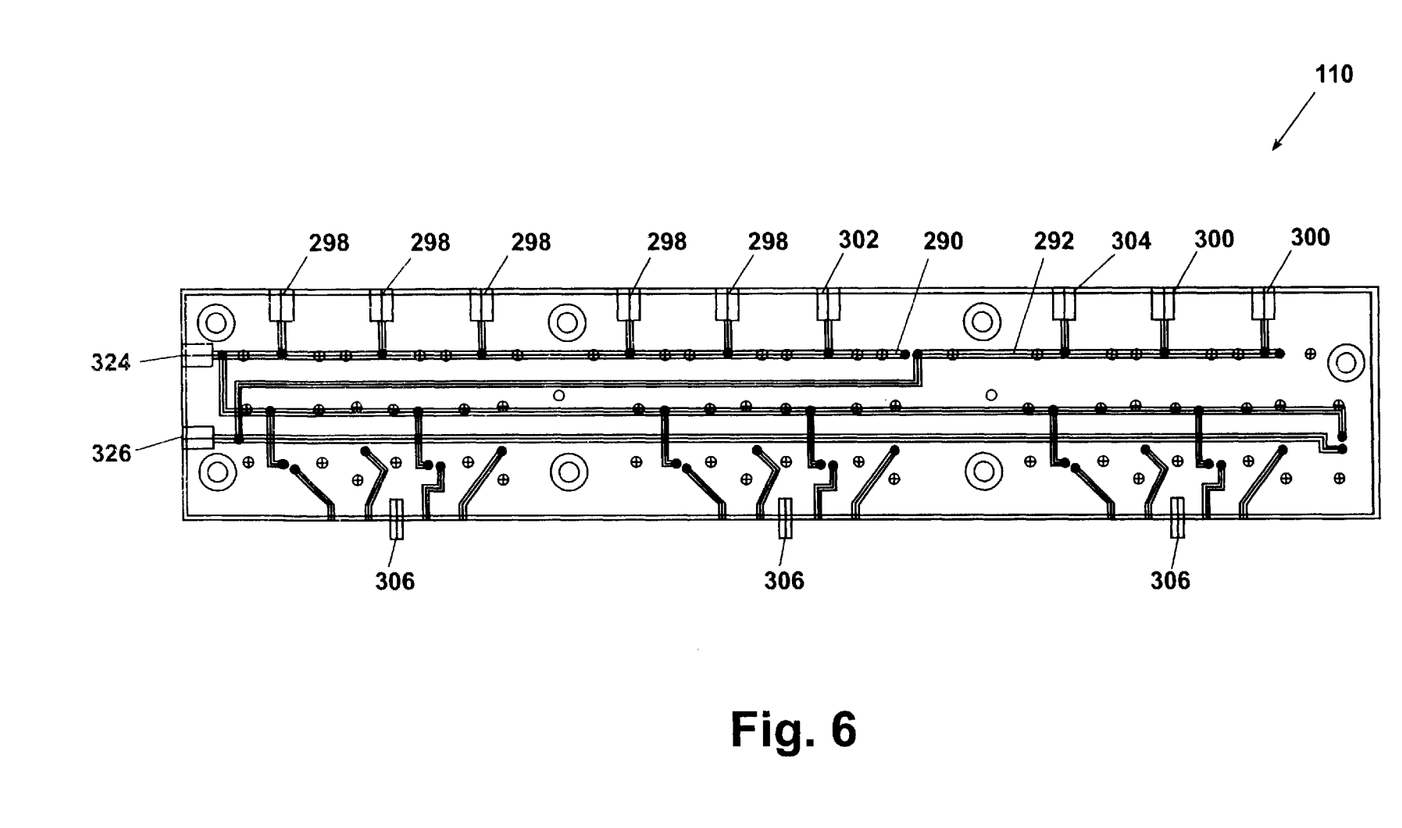
FIG. 6 shows a phantom top view of a master manifold.
Figure 7:
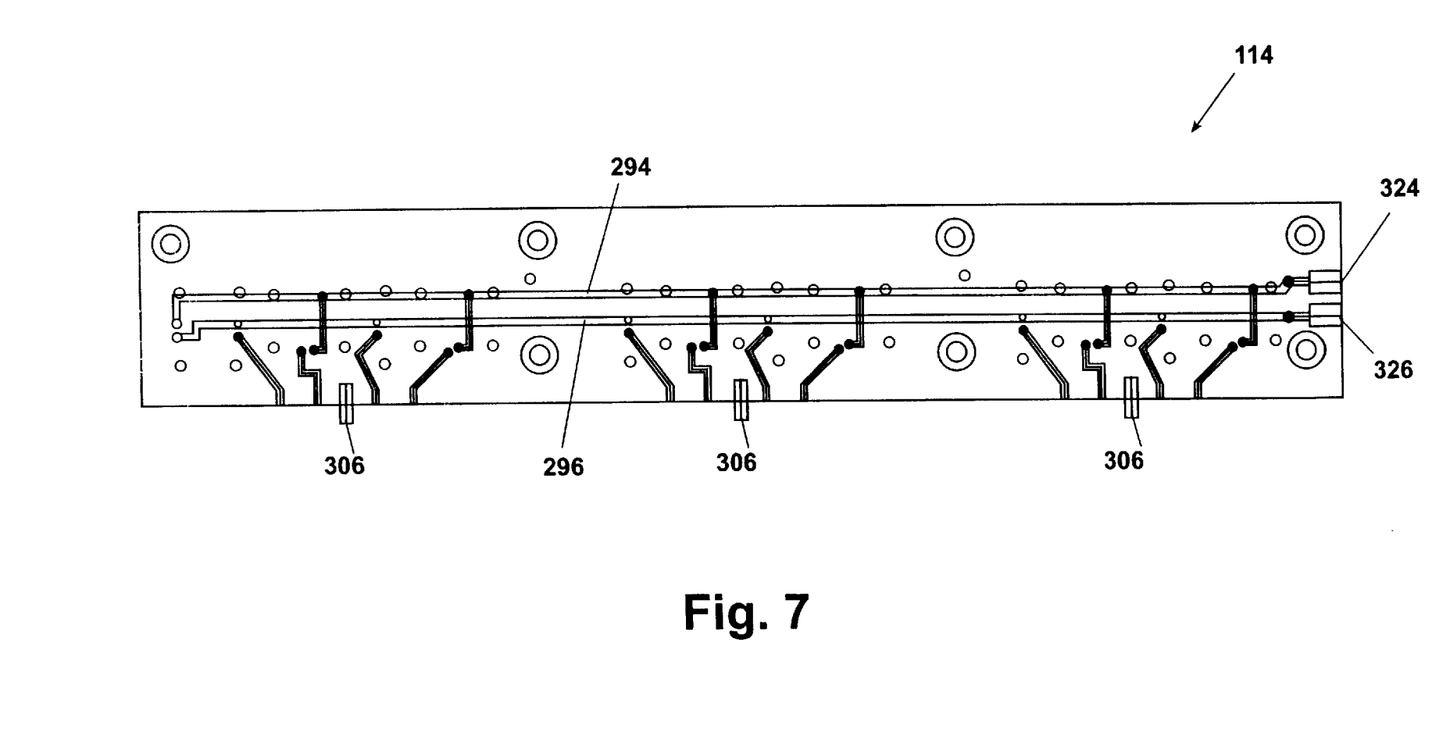
FIG. 7 shows a phantom bottom view of a satellite manifold.

FIG. 6 and FIG. 7 show phantom top and bottom views, respectively, of the master manifold 110 and the satellite manifold 114. Both manifolds 110, 114 are formed from multi-layer, diffusion bonded acrylic, in which channels 290, 292, 294, and 296 are machined into planar surfaces of acrylic layers and the layers are bonded together under heat and pressure. The master manifold 110 is similar to the satellite manifold 114 except that the master manifold 110 provides fluid connections to the liquid reservoirs 118 and waste containers 120 via liquid ports 298 and waste ports 300, respectively. In addition, the master manifold 110 provides fluid connections to filtered ambient air via a gas port 302 and a vent port 304. Locator pins 306 engage the slide cover 150 and the U-shaped tab 196 of the slide carrier 192. The locator pins 306 serve to position the slide cover 150 and slide carrier 192 relative to the manifolds 110, 114.

Returning to FIG. 2, first and second conduits 320, 322 provide fluid communication between the liquid reservoirs 118 and the waste containers 120, respectively, through first and second conduit ports 324, 326. In addition, valves 328, which are mounted on the underside of the master 110 and satellite 114 manifolds, selectively provide fluid communication between the slide cavities and the liquid reservoirs 118, waste containers 120, or ambient air. The valves are under control of the embedded PC module 122, and have zero dead volume to prevent retention of liquid when closed.

Figure 8:
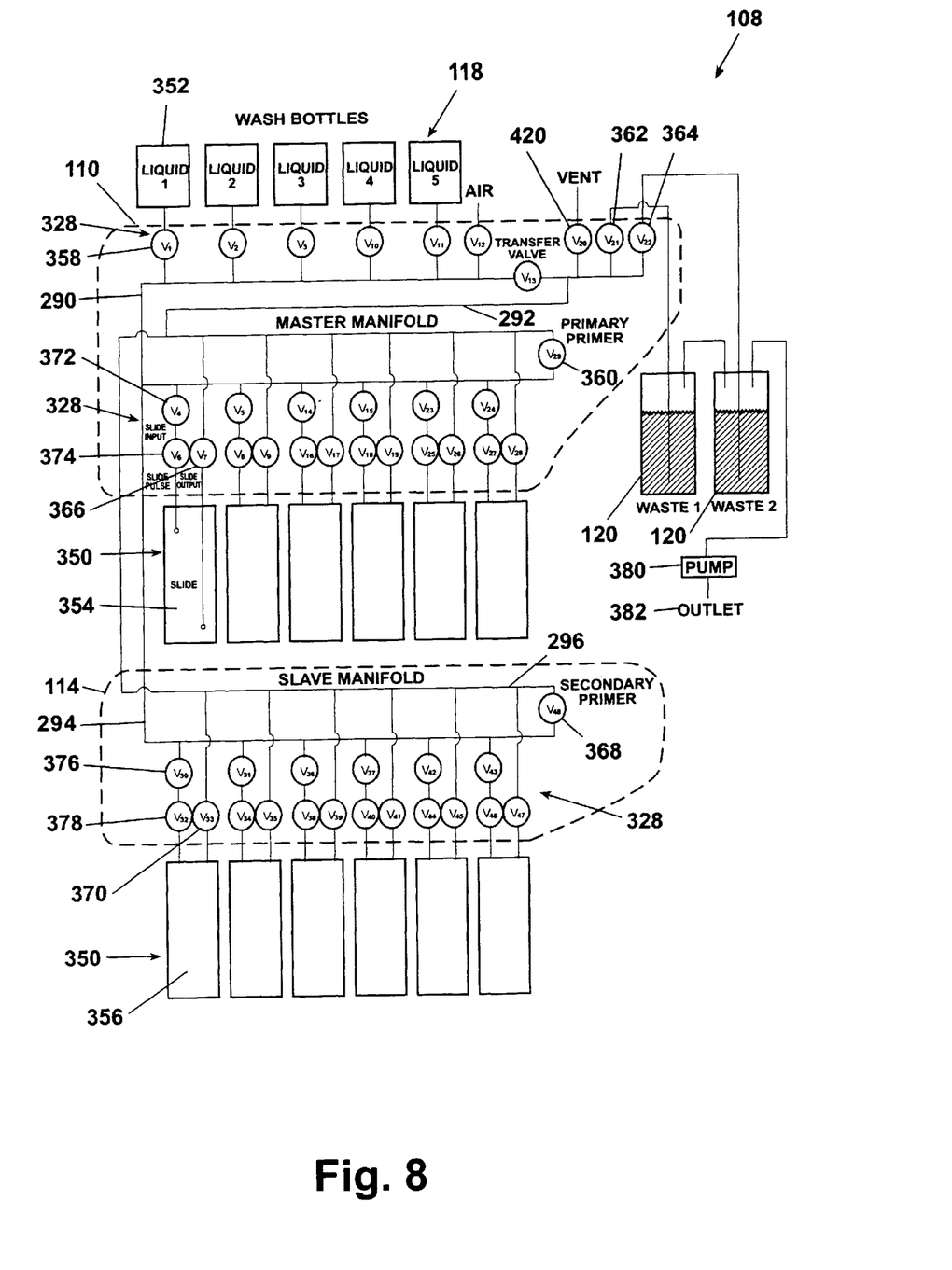
FIG. 8 is a schematic of a fluid control module.

FIG. 8 is a schematic of the fluid control 108 module, and illustrates how fluid moves from the liquid reservoirs 118, through the master manifold 110, the satellite manifold 114, and slide cavities 350, and into the waste containers 120. Before fluid is introduced into the slide cavities 350, a flow path between the liquid reservoirs 118 and the slide cavities 350 is preloaded or primed with liquid from an appropriate reservoir 118. Priming purges any residual fluid remaining from a previous processing step that may contaminate the current processing step.

To illustrate priming, suppose one desires to inject liquid from a first reservoir 352 into a first slide cavity 354 and then into a second slide cavity 356. Initially, all valves 328 are closed. To begin priming, the embedded PC control module 122 (not shown) opens a first liquid input valve 358, a primary primer valve 360, and either a first 362 or a second 364 waste valve, which fills the conduit 290 with liquid from the first reservoir 352 since the waste containers 120 are under vacuum. Next, the control module 122 opens a first slide cavity output valve 366 and closes the primary primer valve 360, which purges the first slide cavity 354 of any residual fluid from a previous processing step. Similarly, to prime the conduit 294 providing fluid communication between the first liquid reservoir 352 and the second slide cavity 356, the embedded PC control module 122 opens the first liquid input valve 358, a secondary primer valve 368, and either the first 362 or the second 364 waste valves. This process fills the conduit 294 with liquid from the first reservoir 352. Next, the control module 122 opens a second slide cavity output valve 370 and closes the secondary primer valve 368, which purges the second slide cavity 356 of any residual fluid from a previous processing step.

Once priming is complete, and all of the valves 328 are closed, the PC control module 122 injects liquid from the first reservoir 352 into the first slide cavity 354 by opening the first liquid input valve 358, a first slide cavity input valve 372, a first slide cavity pulse valve 374, the first slide cavity output valve 366, and either the first 362 or the second 364 waste valves. Similarly, the PC control module 122 injects liquid from the first reservoir 352 into the second slide cavity 356 by opening the first liquid input valve 358, a second slide cavity input valve 376, a second slide cavity pulse valve 378, the second slide cavity output valve 370, and either the first 362 or the second 364 waste valves.

As described above, a vacuum pump 380 maintains vacuum within headspaces of the two waste containers 120. Ambient pressure in the liquid reservoirs 118 and vacuum within the waste containers 120, results in a pressure drop that drives fluid flow throughout the fluid control module 108. As the waste containers 120 fill during processing, headspace within the two waste containers 120 decreases, which diminishes pumping capacity. As a result, the vacuum pump 380 is run continuously to maintain vacuum within the fluid control module under all operating conditions. When the waste container 120 headspace is large, it allows the fluid control module 108 to respond to peak or transient pumping demands. Typically, exhaust 382 from the vacuum pump is channeled to the rear of the apparatus 100. When the exhaust 382 is hazardous, it is piped to a location for disposal. To aid in the handling of hazardous materials, the waste containers 120 can be preloaded with a neutralizing agent.

Figure 9:
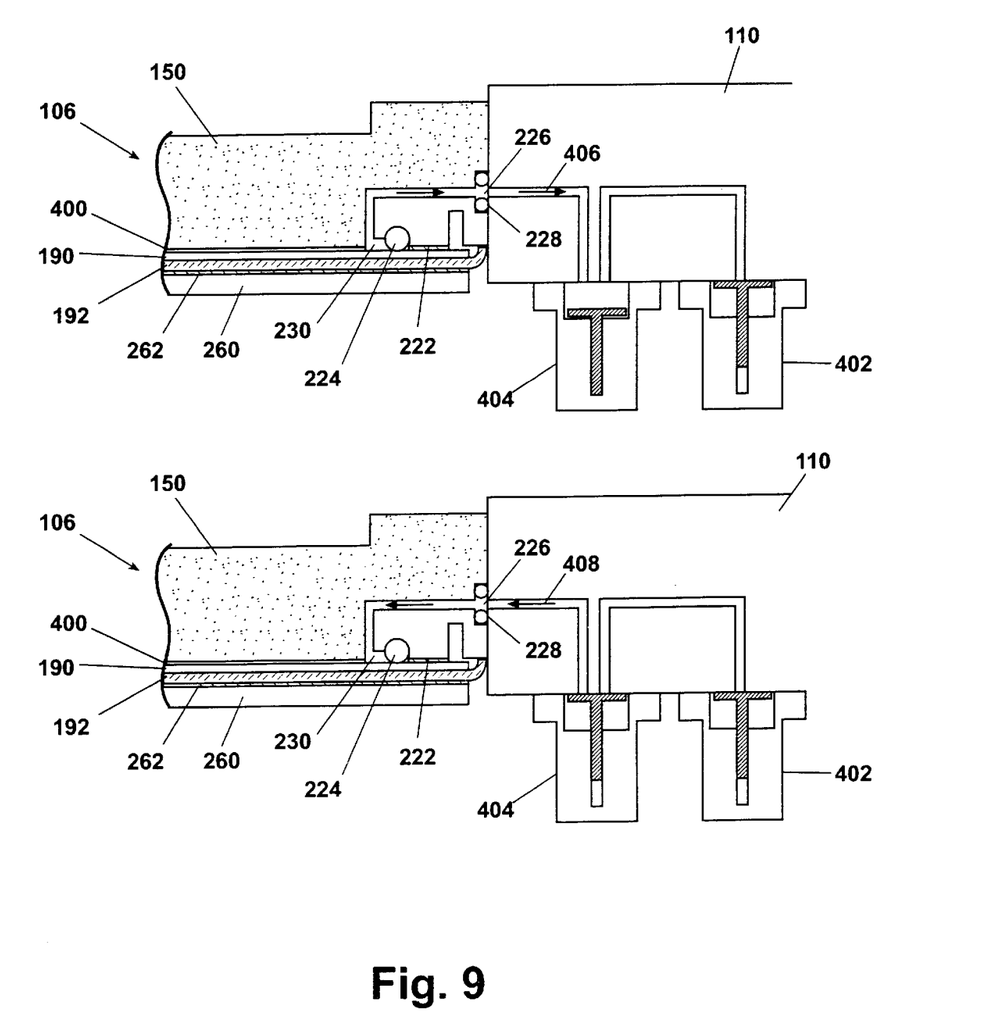
FIG. 9 illustrates fluid agitation within a slide cavity using valve actuation.

FIG. 9 illustrates agitation of fluid 400 within one of the slide cavities 350 by valve actuation. FIG. 9 shows a cross sectional view of one of the slide plate assemblies 106 abutting the master manifold 110. A pair of valves—a slide cavity input valve 402 and a slide cavity pulse valve 404—provide fluid communication with the liquid reservoirs 118. The embedded PC control module 122 (not shown) can agitate the fluid 400 by opening and closing the pulse valve 404. This action draws air out of and into the first diffusion channel 230, as shown by arrows 406, 408. The diffusion channel 230 acts as a pressure reservoir that tends to dampen and distribute pressure forces within the slide cavity 350, which minimizes shearing of any DNA adhering to the slide 190.

Fluid 400 within the slide cavities 350 often gases during heating forming bubbles that tend to collect in the first diffusion channel 230. Gas collection in the first diffusion channel 230 is enhanced by agitation and by the slight incline of the slide plate assembly 106. Intermittent venting of the slide cavity 350 through, for example, an output valve 366, 370 and venting valve 420 (FIG. 8), prevents the gas from pressurizing and displacing fluid 400. Fluid loss by evaporation is minimized by a short vent period.

Temperature Control

Figure 10:
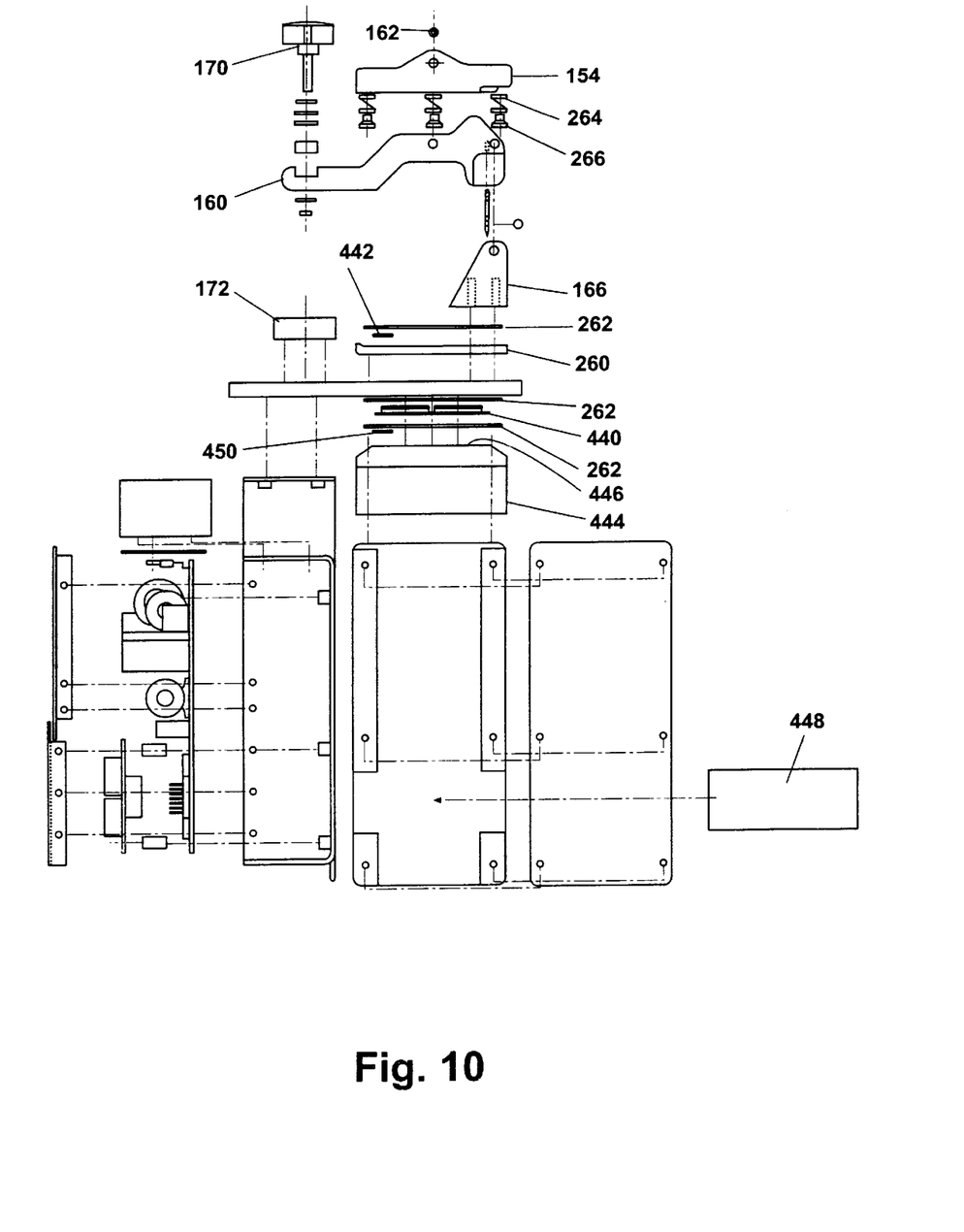
FIG. 10 shows an exploded view of a temperature management module.

FIG. 10 shows an exploded view of the temperature management module 104. The temperature management module 104 includes a thermal plate 260 that is designed and constructed to maximize heat transfer between peltier devices 440 and the glass slides 190 of FIG. 3. The thermal plate 260 is designed to provide rapid temperature response and uniform temperature distribution across the surface of the glass slides 190. To achieve these design goals, the thermal plate 260 has minimal thermal mass and a high degree of flatness to maximize thermal contact area. Where mechanical connections must be made to the thermal plate 260, they are made in positions that do not cause substantial disruption to the temperature profile. The thermal plate 260 is disposed on a graphite-loaded thermal pad 262 that forms a thermal interface between the peltier devices 440 and an anodised surface of the thermal plate 260. A thermal fuse (not shown) is bonded to the thermal plate 260 to prevent the module 104 from overheating. In addition, a PT100 temperature sensor 442 is embedded on the top of the thermal plate 260 in close proximity to the DNA sample (array) 210 of FIG. 4 to improve process control.

Each thermal transfer plate 260 is serviced by four peltier devices 440 connected electrically in series and thermally in parallel to provide low thermal impedance between the thermal plate 260 and heat sink (source) 444. The spatial configuration of the peltier devices 440 allows compression screws (not shown) to pass between them forming a compression assembly (sandwich) with the thermal plate 260 and the heat sink 444 forming opposing sides. The positions of the compression screws provide even compression force across the peltier faces when correct torque settings are applied to the compression screws. Graphite-loaded loaded thermal pads 262 are used to connect the peltier devices 440 to the heat sink 444 and the thermal plate 260.

A mating face 446 of the heat sink (source) 444 has a high degree of flatness to maximize thermal contact area with the peltier devices 440. Optimal thermal transfer to incident airflow is achieved using an efficient fin assembly (not shown) coupled to turbulent air flow preconditioned to have zero "dead zones." Preconditioning is achieved by moving a fan 448 a selected distance from the heat sink's 444 fins, which disrupts dead zones created by the fan's 448 stator. A temperature sensor 450 is imbedded in the heat sink 444 to supply temperature data to the embedded PC control module 122.

Each thermal module is typically capable of temperature ramp rates of about 1° C./s, and can control temperature between about 1° C. and 100° C. Ramp rates are taken with the surface of a slide 190 in a dry condition measured on the top surface of the slide 190.

Figure 11:
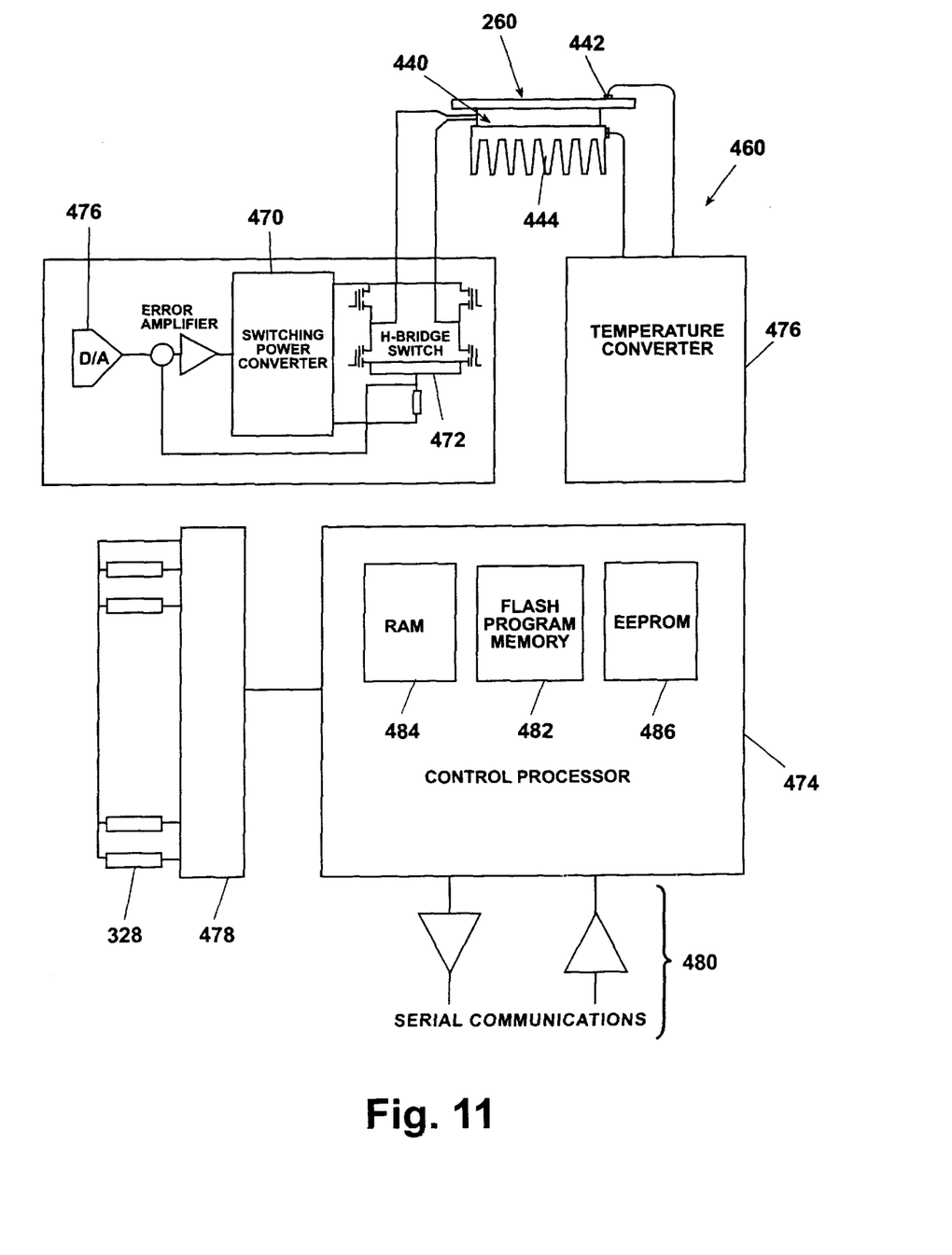
FIG. 11 shows a schematic diagram of a control subsystem for each of the thermal management modules.

FIG. 11 shows a schematic diagram of the thermal management module 104 control subsystem 460. Thermal control of the sample area (DNA array) 210 of the slides 190 depends on accurate and responsive control of the peltier 440 devices. The magnitude and direction of the electrical current input into each of the peltier devices 440 controls the amount and direction of heat transfer across the devices 440. A switching power converter 470 coupled with an H-bridge reversing switch 472, supplies the necessary current. Current is under control of a computer processor 474 via a digital to analog (D/A) converter 476. The temperature of the thermal plate 260 and heat sink (source) 444 is monitored using PT 100 sensors 442 and a temperature converter 476 makes the result available to the processor 474. Electrical current polarity and flow are controlled using the computer processor 474 that in turn monitors temperatures on the thermal plate 260 and the heat sink (source) 444 to calculate applied current and polarity to achieve the demand temperature. A pulse output If from the heat sink 444 fan 448 is monitored to provide warning of air flow failure.

A solenoid valve driver 478 provides a link between the computer processor 474 and the valves 328. In addition, a serial communication interface 480 provides a link between the computer processor 474 and the embedded PC control module 122. The embedded PC control module 122 carries out scheduling of valve 328 operations and temperature changes.

Valve state and temperature change commands are sent to the thermal management module 104 via the serial communications interface 480. The processor 474 in the thermal management module 104 is responsible for direct valve 328 operation and temperature control. For optimum processing, the latter needs to apply rapid temperature changes, quickly stabilizing at the new temperature with no overshoot. This is achieved in the present embodiment using a modeling technique, rather than a traditional proportional-integral-differential (PID) control loop.

The thermal module 104 runs a program that implements a model of the thermal characteristics of the combination of the heat sink 444, peltier device 440, thermal plate 260 and slides 190. Heat pumping is modeled as a fixed transient response (of heat pump rate as a function of time), pumping efficiency (steady-state pump rate as a function of peltier current) and heat loss/gain from the thermal plate 260, through the peltier device 440 to the heat sink 444. The control algorithm predicts the expected thermal plate 260 temperature at a fixed time in the future (typically 5 secs) on the basis of the history of current through the peltier device 440, thermal plate temperature 260 and heat sink 444 temperature. From this, the required (assumed constant) current to achieve the desired current is calculated. After ensuring that the calculated current will fall within the range for the power converter and peltier device 440 and that rate-of-change of temperature will not result in thermal shock damage to the peltier device 440, the calculated current is applied to peltier device 440 by control of the power converter 470 and reversing switch 472. This current is recalculated at a fixed period of around 1 second. Once the thermal plate 260 temperature is close to the target, fine temperature control is done by trimming the assumed thermal conductivity of the peltier device 440, according to the temperature error.

Three types of memory are built into the thermal module processor system different contents:

Flash 482: A boot-loader program;

RAM 484: Operating program and variables;

EEPROM 486: Characteristics of a particular thermal management module 104 (serial number, temperature calibration factors). The boot loader program runs at power-on, its purpose is to accept new program code that is sent to all of the controllers 474 in the thermal modules 104 by the embedded PC control module 122. This is a convenience since the operating code for the thermal modules 104 is stored in the embedded PC control module 122, allowing easy upgrade of instruments in the field.

The six thermal management modules 104 connect via an internal network designed to pass information between the embedded PC control module 122 and the addressed thermal control module 104 (control processor 474). Such information includes operating code passed to the thermal management modules 104, commands, monitored datea, and claibration data.

What is claimed is:

1. An apparatus for automatically hybridizing a DNA microarray immobilized on a surface of a solid substrate, the apparatus comprising:

at least one assembly for securing the solid substrate during hybridization, the assembly comprising a carrier and a removable cover having a surface facing the carrier, the carrier and the removable cover dimensioned to receive the solid substrate between the carrier and the surface of the removable cover so that the surfaces of the removable cover and the solid substrate define a cavity;

a fluid control module comprising a fluid manifold, at least one liquid reservoir, at least one waste container, a pulse valve in fluid communication with a diffusion channel opening into the cavity, and a vacuum source in fluid communication with the waste container, the fluid manifold providing fluid communication between the liquid reservoir and the cavity and between the cavity and the waste container, and the vacuum source providing a pressure drop between the liquid reservoir and the waste container, wherein the pressure drop drives fluid flow throughout the fluid control module and the pulse valve provides for agitation of fluid within the cavity;

at least one thermal management module for controlling temperature of the DNA microarray immobilized on the surface of the solid substrate, the thermal management module thermally contacting the assembly.

2. An apparatus for automatically hybridizing a DNA microarray immobilized on a surface of a solid substrate, the apparatus comprising:

at least one assembly for securing the solid substrate during hybridization, the assembly comprising a carrier and a removable cover having a surface facing the carrier, the carrier and the removable cover dimensioned to receive the solid substrate between the carrier and the surface of the removable cover so that the surfaces of the removable cover and the solid substrate define a cavity;

a fluid control module comprising a fluid manifold, at least one liquid reservoir, at least one waste container, and a vacuum source in fluid communication with the waste container, the fluid manifold providing fluid communication between the liquid reservoir and the cavity and between the cavity and the waste container, and the vacuum source providing a pressure drop between the liquid reservoir and the waste container, wherein the pressure drop drives fluid flow throughout the fluid control module; and at least one thermal management module for controlling temperature of the DNA microarray immobilized on the surface of the solid substrate, the thermal management module thermally contacting the assembly;

wherein the removable cover has first and second diffusion channels opening into the cavity, the first and second diffusion channels in fluid communication with the fluid manifold, and the fluid control module includes a pulse valve in fluid communication with the first diffusion channel for agitating fluid within the cavity.

3. The apparatus of claim 2, wherein the apparatus includes at least two assemblies for securing solid substrates during hybridization.

4. The apparatus of claim 3, wherein the apparatus includes at least two thermal management modules.

5. The apparatus of claim 4, wherein each of the thermal management modules thermally contact different assemblies.

6. The apparatus of claim 2, wherein the apparatus includes at least six assemblies for securing solid substrates during hybridization.

7. The apparatus of claim 6, wherein the apparatus includes at least six thermal management modules.

8. The apparatus of claim 7, wherein each of the thermal management modules thermally contact different assemblies.

9. The apparatus of claim 2, further comprising a shim removably disposed between the surface of the solid substrate and the removable cover, the shim defining a standoff between the surface of the removable cover and the surface of the solid substrate.

10. The apparatus of claim 9, wherein the shim has a cut-out demarcating an inner periphery, the inner periphery of the shim encompassing a smaller area than the surface of the solid substrate.

11. The apparatus of claim 10, further comprising an o-ring contained in a groove on the surface of the removable cover, the grove located adjacent the inner periphery of the shim.

12. The apparatus of claim 11, wherein the o-ring is fabricated from a perfluoroelastomer.

13. The apparatus of claim 2, wherein the removable cover is fabricated from a high-temperature plastic.

14. The apparatus of claim 13, wherein the high temperature plastic is polysulfone.

15. The apparatus of claim 2, wherein the first and second diffusion channels provide for fluid flow into and out of the cavity.

16. The apparatus of claim 15, wherein the first and second diffusion channels are spaced apart so that fluid entering and exiting the cavity via the first and second diffusion channels flows across the DNA microarray immobilized on the surface of the solid substrate.

17. The apparatus of claim 2, further comprising a port located in the removable cover for manually injecting liquids directly into the cavity.

18. The apparatus of claim 17, wherein the port is tapered.

19. The apparatus of claim 17, wherein the port is dimensioned to receive a pipette.

20. The apparatus of claim 17, wherein the port is in fluid communication with the second diffusion channel.

21. The apparatus of claim 20, wherein the assembly for containing the solid substrate is tilted upward from the second diffusion channel towards the first diffusion channel.

22. The apparatus of claim 2, wherein the removable cover includes thermal breaks for reducing distortion resulting from thermal gradients in a direction parallel to the surface of the solid substrate.

23. The apparatus of claim 2, wherein the carrier includes tabs for reducing lateral movement of the solid substrate.

24. The apparatus of claim 2, wherein the carrier is fabricated from stainless steel.

25. The apparatus of claim 2, wherein the removable cover and the carrier are adapted to secure at least two solid substrates.

26. The apparatus of claim 2, wherein the fluid manifold comprises multiple layers of acrylic.

27. The apparatus of claim 2, wherein the fluid control module includes valves providing selective fluid communication between the liquid reservoir and the cavity and between the cavity and the waste container.

28. The apparatus of claim 27, wherein the valves are zero dead volume valves.

29. The apparatus of claim 2, wherein the fluid control module includes at least two waste containers.

30. The apparatus of claim 2, wherein the vacuum source is a vacuum pump.

31. The apparatus of claim 2, wherein the thermal management module includes at least one Peltier device in thermal contact with the assembly.

32. The apparatus of claim 31, wherein the thermal management module includes a thermal plate disposed between the assembly and the Peltier device.

33. The apparatus of claim 31, wherein the thermal management module includes a graphite-loaded pad disposed between the assembly and the Peltier device.

34. The apparatus of claim 33, wherein the thermal management module includes a thermal plate disposed between the assembly and the graphite-loaded pad.

35. The apparatus of claim 2, wherein the thermal management module includes at least four Peltier devices in thermal contact with the assembly.

36. The apparatus of claim 2, wherein the thermal management module includes at least one temperature sensor located adjacent the carrier.

37. The apparatus of claim 2, wherein the thermal management module is capable of temperature ramp rates of about one ° C. per second.

38. The apparatus of claim 2, wherein the thermal management module is capable of controlling the temperature of the DNA microarray between about one ° C. and about one hundred ° C.

39. The apparatus of claim 2, further comprising an embedded personal computer communicating with the fluid control module.

40. The apparatus of claim 2, further comprising an embedded personal computer communicating with the thermal management module.

41. The apparatus of claim 40, further comprising software running on the embedded personal computer, the software controlling the thermal management module using a mathematical model that approximates thermal characteristics of the thermal management module.

42. The apparatus of claim 2, further comprising a power supply module providing electrical current to the fluid control module and thermal management module.

43. The apparatus of claim 42, wherein the power supply module uses intelligent energy scheduling.

44. An apparatus for automatically hybridizing DNA microarrays, the apparatus comprising:

a solid substrate having a DNA microarray immobilized on a surface of the solid substrate;

at least one assembly for securing the solid substrate during hybridization, the assembly comprising a carrier and a removable cover having a surface facing the carrier, the carrier and the removable cover dimensioned to receive the solid substrate between the carrier and the surface of the removable cover so that the surfaces of the removable cover and the solid substrate define a cavity;

a fluid control module comprising a fluid manifold, at least one liquid reservoir, at least one waste container, a pulse valve in fluid communication with a diffusion channel opening into the cavity, and a vacuum source in fluid communication with the waste container, the fluid manifold providing fluid communication between the liquid reservoir and the cavity and between the cavity and the waste container, and the vacuum source providing a pressure drop between the liquid reservoir and the waste container, wherein the pressure drop drives fluid flow throughout the fluid control module and the pulse valve provides for agitation of fluid within the cavity;

at least one thermal management module for controlling temperature of the DNA microarray immobilized on the surface of the solid substrate, the thermal management module thermally contacting the assembly.

* * * * *